(12) United States Patent
Potter et al.

(10) Patent No.: US 6,326,366 B1
(45) Date of Patent: Dec. 4, 2001

(54) HORMONE REPLACEMENT THERAPY

(75) Inventors: Susan M. Potter, Ellisville; Edna C. Henley, St. Louis; Richard B. Taylor, Valley Park, all of MO (US)

(73) Assignee: Protein Technologies International, St. Louis, MO (US)

( * ) Notice: Subject to any disclaimer, the term of this patent is extended or adjusted under 35 U.S.C. 154(b) by 0 days.

(21) Appl. No.: 09/643,429

(22) Filed: Aug. 22, 2000

(51) Int. Cl.$^7$ .................................................... A61K 31/56

(52) U.S. Cl. ........................................... 514/182; 514/456

(58) Field of Search ..................................... 514/182, 456

(56) References Cited

U.S. PATENT DOCUMENTS

| | | | |
|---|---|---|---|
| 4,894,373 | 1/1990 | Young | 514/239.2 |
| 5,424,331 | 6/1995 | Shlyankevich | 514/456 |
| 5,498,631 | 3/1996 | Gorbach et al. | 514/456 |
| 5,506,211 | 4/1996 | Barnes et al. | 514/27 |
| 5,516,528 * | 5/1996 | Hughes et al. | 424/464 |
| 5,569,459 | 10/1996 | Shlyankevich | 424/195.1 |
| 5,654,011 | 8/1997 | Jackson et al. | 424/635 |
| 5,733,926 | 3/1998 | Gorbach | 514/456 |
| 5,830,887 * | 11/1998 | Kelly | 514/182 |
| 5,952,374 | 9/1999 | Clarkson, Jr. et al. | 514/456 |
| 6,001,368 | 12/1999 | Jenks | 424/195.1 |
| 6,086,915 * | 7/2000 | Zeligs et al. | 424/455 |

FOREIGN PATENT DOCUMENTS

| | | |
|---|---|---|
| 3430799A1 | 8/1983 | (DE) . |
| 59-199630A | 4/1983 | (JP) . |
| 1-258669 | 4/1988 | (JP) . |

OTHER PUBLICATIONS

Satchell et al, AM. J. Clin. Nutr., vol. 40, #3, pp. 569–578 (abstract), Sep. 1984.*
Ingram, Lancet, Oct. 4, 1997.*
Duncan et al, Cancer Epidemiol. Biomarkers Prev., vol. 19, #6, pp. 581–586 (abstract), Jun. 2000.*
Adlercreutz et al, J. Steriod Biochem., vol. 25, pp. 791–797 (abstract), Nov. 1986.*
Soybean Utilization, Chapter 2—Morphology and Composition, pp. 64–66 (1987).
Barnes et al., Soybeans Inhibit Mammary Tumors in Models of Breast Cancer, *Mutagens and Carcinogens in the Diet*, Wiley–Liss, (1990), pp. 239–253.
Anthony et al., Soybean Isoflavones Improve Cardiovascular Risk Factors Without Affecting the Reproductive System of Peripubertal Rhesus Monkeys, *Journal of Nutrition*, (1996), vol. 126, No. 1, pp. 43–50.
Wilcox et al., Thrombotic Mechanisms in Atherosclerosis: Potential Impact of Soy Proteins, *Journal of Nutrition*, (1995), vol. 125, Supp. 3, pp. 631s–638s.
Raines et al., Biology of Atherosclerotic Plaque Formation: Possible Role of Growth Factors in Lesion Development and the Potential Impact of Soy, *Journal of Nutrition*, (1995), vol. 125, Supp. 3, pp. 624s–630s.
Blair et al., Variable Effects of Tyrosine Kinase Inhibitors on Avian Osteoclastic Activity and Reduction of Bone Loss in Overectomized Rats, *J. of Cellular Biochemistry*, (1996), vol. 64, No. 4, pp. 629–637.
Grabiel et al., Subject Compliance Assessed by Excretion of Genistein, *FASEB J.*, (1995), vol. 9, No. 4, abstract A994.
Zava et al., Effects of Plant and Fungal Estrogens on E–Sensitive Human Breast Cancer Cells, *Annual Meeting Am. Assoc. Cancer Res.*, (1994), vol. 35, abstract A525.
Anderson et al., Orally Dosed Denistein from Soy and Prevention of Cancellous Bone Loss in Two Overectimized Rat Models, *Journal of Nutrition*, (1995), vol. 125, No. 3, Supp., p. 799s.
Bohm et al., Health Relevance of Soya Beans Due to Their Isoflavonoid Content, *Lebensmittelwirtsch*, (1996), vol. 47, No. 12, pp. 55–57.
Knight et al, A Review of Phytoestrogens and Their Effects in Relation to Menopausal Symptoms, *Aust. J. Nutr. Diet*, (1996), vol. 53(1), pp. 5–11.
Clarkson et al., The Nonhuman Primate Model of the Relationship Between Gonadal Steroids and Coronary Heart Diseases, *Progress in Cardiovascular Diseases*, (1995), vol. 38/3, pp. 189–198.
Setchell et al., Dietary Estrogens—A Probable Cause of Infertility and Liver Disease in Captive Cheetahs, *Gastroenterology*, (1987), vol. 93, (2), pp. 225–233.
Cline et al., Effects of Hormonal Therapies and Dietary Soy Phytoestrogens on Vaginal Cytology in Surgically Postmenopausal Macques, *Fertility and Sterility*, (1996), vol. 65/5, pp. 1031–1035.
Wilcox et al., Ostrogenic Effects of Plant Foods in Postmenopausal Women, *Br. Med. J.*, (1990), vol. 301, pp. 905–906.

(List continued on next page.)

*Primary Examiner*—James H. Reamer
(74) *Attorney, Agent, or Firm*—Richard B. Taylor

(57) ABSTRACT

The present invention relates to a hormone replacement therapy, and a composition useful therein, for women having reduced levels of endogenous estrogen. A mammalian estrogen and an isoflavone which is incapable of being metabolized to equol are co-administered to a woman having a reduced level of endogenous estrogen. The hormone replacement therapy is effective to inhibit or prevent diseases or conditions resulting from, or exacerbated by, a reduction in endogenous estrogen including: coronary heart disease, cardiovascular disease, osteoporosis, loss of cognitive function, urinary incontinence, weight gain, fat mass gain, and vasomotor symptoms. A composition for use in the hormone replacement therapy of the present invention contains a mammalian estrogen and at least one isoflavone, where the isoflavone is incapable of being metabolized to equol by a human, and where the composition contains less than 10% by weight of isoflavones and phytoestrogens capable of being metabolized to equol by a human.

37 Claims, 3 Drawing Sheets

OTHER PUBLICATIONS

Certain Plant Compounds Can Affect Women's Health, *Healthline*, (1992), pp. 12–14.

Wahlqvist et al., Soybean Products.

Price et al., Naturally Occurring Oestrogens in Foods—a Review, *Food Additives and Contaminatnts*, (1985), vol. 2, No. 2, pp. 73–106.

Miksicek, Commonly Occurring Plant Flavanoids Have Estrogenic Activity, *Molecular Pharmacology*, (1993), vol. 44(1), pp. 37–43.

Molteni et al., In Vitro Hormonal Effects of Soybean Isoflavones, *Journal of Nutrition*, (1995), vol. 125/3 Supp. pp. 751S–56S.

Kelly et al., The Variable Metabolic Response to Dietary Isoflavones in Humans, *Proceedings of the Society for Experimental Biology and Medicine*, (1995), vol. 208 (1), pp. 40–43.

Joannou et al., A Urinary Profile Study of Dietary Phytoestrogens. The Identification and Mode of Metabolism of New Isoflavonoids, *J. Steroid Biochem. Molec.Biol.*, (1995), vol. 54, No. 3–4, pp. 167–184.

Murphy et al., Total Genistein and Daidzein Content of Soyfoods, *Food Composition*, Abstract 4283.

Setchell et al., Naturally Occurring Non–Steroidal Estrogens of Dietary Origin, *Estrogens in the Environment, J. McLachlen, Editor*, pp. 69–85.

Axelson et al., Soya—a Dietary Source of the Non–Steroidal Oestrogen Equol in Man and Animals. *J. Endocr.*, (1984), vol. 102, pp. 49–56.

Anthony et al., Soybean Isoflavones Improve Cardiovascular Risk Factors Without Affecting the Reproductive System of Peripubertal Rhesus Monkeys, accepted for publication in *The Journal of Nutrition*, (Aug. 16, 1995), 125:799S.

* cited by examiner

HORMONE REPLACEMENT THERAPY

FIELD OF THE INVENTION

The present invention relates to a composition and a method for reducing the risk of coronary heart disease, osteoporosis, loss of cognitive function, urinary incontinence, weight and fat mass gain, and vasomotor symptoms in women having a reduced level of endogenous estrogen. In particular, a combination of a mammalian estrogen and an isoflavone are used in a hormone replacement therapy regimen, where the isoflavone is incapable of being metabolized to equol by a human.

BACKGROUND OF THE INVENTION

Estrogen plays an important role in protecting the health of women. It has been implicated as a significant factor in protecting and maintaining cardiovascular health, bone mass, and mental cognition. The health protective effects of estrogen for women have been proposed as one of the reasons that women in the United States live an average of 7½ years longer than men. Women form 59% of the U.S. population over age 65 and 72% of the population over age 85.

A woman's endogenous level of estrogen is significantly reduced upon entering menopause or upon premature surgical menopause induced by removal of the uterus and/or ovaries. The amount of a woman's endogenous estrogen is typically reduced to less than 10% of premenopausal levels following natural or surgical menopause. This reduction of endogenous estrogen levels results in the loss of estrogen's health protective effects, particularly with respect to cardiovascular health, bone health, and mental cognition.

Cardiovascular disease is the leading cause of death in women. Compared to men, premenopausal women are relatively protected from cardiovascular disease by estrogen, but gradually lose this protection following menopause as estrogen levels decline. Patterns in Coronary Heart Disease—Morbidity and Mortality in the Sexes: A 26-Year Follow-Up of the Framingham Population, Lerner & Kannel, *Amer. Heart J.*, 111: 383–90 (1986). The onset of cardiovascular disease is hastened in women by prematurely induced surgical menopause and its attendant reduction in endogenous estrogen levels. Time Interval from Castration in Premenopausal Women to Development of Excessive Coronary Atherosclerosis, Parrish, H. M. et al., *Amer. J. Obst. Gynecol.*, 99: 155–62 (1967).

Osteoporosis, while not a leading cause of mortality in post-menopausal women, is a substantial contributor to morbidity in such women. Osteoporosis is present in approximately one in four women over the age of 65, and typically develops after post-menopausal reduction of endogenous estrogen. Loss of bone mineral density, the key indicator of osteoporosis, is also hastened by prematurely induced surgical menopause and its attendant reduction in endogenous estrogen levels. Relative Contributions of Aging and Estrogen Deficiency to Postmenopausal Bone Loss, Richeson, L. S. et al., N. *Eng. J. Med.*, 311: 1273–75 (1984).

Loss of cognitive function is also significantly more likely to occur in postmenopausal women as a result of the loss of the protective effects of estrogen. Loss of cognitive function is associated with decreased choline acetyltransferase ("ChAT") and the loss of cholinergic neurons. Estrogen has been identified as an agent which upregulates ChAT production, thereby inhibiting the loss of cognitive function associated with decreased ChAT. Ovarian Steroid Deprivation Results in a Reversible Learning Impairment and Compromised Cholinergic Function in Female Sprague-Dawley Rats, Singh et al., *Brain Research*, 644: 305–12 (1994).

The reduction of endogenous estrogen as a result of natural or surgical menopause also has other deleterious health effects. Reduced estrogen levels have been implicated in the development of urinary incontinence as a result of the effect of the loss of estrogen on the smooth muscle cells of the urethra. Reduced estrogen levels are also implicated in significant weight and fat mass gain in postmenopausal women. Impact of Hormone Replacement Therapy on the Body Mass and Fat Compositions of Menopausal Women: A Cross-Sectional Study, Sayegh, R. et al., *Menopause*, Vol. 6, No. 4, 312–15 (1999).

Hormone replacement therapy is currently utilized as a treatment to increase the level of estrogen in women having reduced levels of endogenous estrogen resulting from natural or surgical menopause. Supplemental estrogen is provided to the women in order to inhibit, ameliorate, or prevent diseases or conditions which result from the reduction of endogenous estrogen.

The estrogen provided in hormone replacement therapy is particularly useful to ameliorate the diseases and conditions noted above-cardiovascular disease and coronary heart disease, osteoporosis, declining mental cognition, urinary incontinence, and weight and fat mass gain in postmenopausal women, as well as inhibiting vasomotor symptoms resulting from a reduction in endogenous estrogen such as hot flush. Administration of unopposed conjugated estrogen has been found to reduce the relative risk of coronary disease in postmenopausal women to a level of 0.41 to 0.56 that of untreated postmenopausal women. Estrogen Replacement Therapy and Coronary Disease: A Quantitative Assessment of the Epidemiological Evidence, Stampfer & Colditz, *Prev. Med*, 20: 47–63 (1991). Unopposed estrogen has been shown to prevent menopausal bone loss at a number of skeletal sites, and tends to maintain bone mass at the level present when administration is initiated. Long Term Prevention of Post-Menopausal Osteoporosis by Estrogen, R. Lindsay et al., *Lancet*, 1: 1038–41 (1976); HRT and Osteoporosis, J. Compston, *Brit. Med Bull.*, 48: 304–44 (1992). As a result, estrogen is regarded as a first-line therapy for postmenopausal women having reduced bone mineral density. Treatment of postmenopausal women with unopposed estrogen has also been shown to have beneficial effects on cognitive function by maintaining short term memory and ameliorating clinical symptoms of Alzheimer's disease. The Influence of Estrogens On the Psyche In Climacteric and Post-Menopausal Women, Furuhjelm & Fedor-Freybergh, *Consesus on Menopause Research*, Van Keep, Greenblatt, & Albeaux-Fernet (eds.), University Park Press, Baltimore, 84–93 (1976); Estrogen and/or Androgen Replacement Therapy and Cognitive Functioning in Surgically Menopausal Women, B. Sherwin, *Psychoneuroendocrinology*, 13: 345–47 (1988); Estrogen and Memory in Postmenopausal Women; B. Sherwin, Third Annual Meeting, North American Menopause Society, 50 (1992); Senile Dementia-Alzheimer's Type and Estrogen, Honjo et al., *Hormone Metab. Res.*, 27: 204–07 (1995). Hormone replacement therapy is also indicated to treat vasomotor symptoms such as hot flush, which are associated with a decrease in endogenous estrogen levels in women. Determining the Role of Long-Term Hormone Therapy After Menopause in the Context of Primary Preventive Health Care for Women, Wolf H. Utian, *Menopause*, Vol. 3, No.2, 65–70 (1996).

Unfortunately, administration of unopposed estrogen to postmenopausal women presents serious health risks. Estrogen has a stimulatory effect on the growth of uterine and breast tissues, and treatment of postmenopausal women with estrogen is associated with significant increases in uterine and breast cancer. Unopposed estrogen users are 3–6 times more likely than non-users to develop endometrial cancer after 3–10 years of use, and are 10 times more likely to develop endometrial cancer after 10 years of use. Hormone Replacement and Cancer, E. Barrett-Conner, *Brit. Med. Bull.*, 48:345–55 (1992). Administration of estrogen over a long period of time, e.g. 10–15 years, is associated with a 30–50% increase in the risk of breast cancer, although short term administration of estrogen, e.g. less than 5 years, appears to have no adverse effects. Selective Estrogen Receptor Modulators, Kauffman & Bryant, *DN&P*, 8(9): 531–539 (November 1995).

Currently prescribed hormone replacement therapies utilize a progestin which is co-administered with estrogen to limit the estrogen's uterine stimulatory effects, thereby reducing the risk of endometrial cancer. Addition of progestin, however, does not reduce the increased risk of breast cancer induced by administration of estrogen. The Use of Estrogens and Progestins and the Risk of Breast Cancer in Postmenopausal Women, G. Colditz et al., *N. Eng. J. Med.*, 332: 1589–93 (1995). Furthermore, co-administration of progestin has several undesirable side-effects such as continuing menstrual periods, cyclic depression, edema, lower abdominal cramps, breast tenderness, and symptoms like premenstrual syndrome. The disincentives of progestin induced side-effects and the fear of breast cancer combine to 1) substantially reduce the number of postmenopausal women choosing to start a hormone replacement therapy treatment, and 2) once a hormone replacement therapy is started, result in poor compliance with the hormone replacement therapy over an extended period of time, and ultimately, a discontinuance of the therapy.

U.S. Pat. No. 5,516,528 to Hughes et al. provides a novel hormone replacement therapy in which soy derived phytoestrogens are utilized in combination with estrogen, instead of progestin. The soy derived phytoestrogens are selective estrogen receptor modulators which have both estrogenic and anti-estrogenic activity, and act as estrogen antagonists in both uterine and breast tissues. The phytoestrogens, therefore, serve to decrease the risk of both estrogen induced uterine and breast cancers in the hormone replacement therapy. The phytoestrogens have estrogenic activity outside of breast and uterine tissues, and supplement estrogen's cardioprotective effects and bone mineral maintenance effects. The phytoestrogens do not produce the undesirable side effects of progestin such as continuing menstrual periods, breast tenderness, abdominal cramping, or cyclic depression. Therefore, the phtyoestrogen/estrogen hormone replacement therapy offers the benefits of estrogen while reducing the risk of estrogen induced breast and uterine cancer without undesirable side effects which reduce compliance with a hormone replacement therapy utilizing a progestin.

As promising as the phytoestrogen/estrogen hormonal replacement therapy disclosed in the '528 patent appears, it suffers a significant defect. Specifically, the phytoestrogens utilized in the hormone replacement therapy include isoflavones such as daidzein, formononetin, and their glycosides and glycoside conjugates which are metabolized by humans to equol. While less estrogenic than estrogen, equol is substantially more estrogenic than its isoflavone phytoestrogen precursors, and may induce estrogenic-like tissue growth in the breast and uterus. Therefore, inclusion of phytoestrogens which can be metabolized to equol in a phytoestrogen/estrogen hormone replacement therapy is at best counterproductive to the phtyoestrogenic inhibition of estrogen induced breast and endometrial cancer, and at worst actually enhances tissue proliferative estrogenic effects in breast and uterine tissues.

Equol may present a particular problem at the levels of phytoestrogen administration required in the hormone replacement therapy disclosed in the '528 patent. Human consumption of 40 grams of soy per day (containing approximately 120 mg of phytoestrogens) has been shown to increase the urinary levels of equol as much as 1000 fold higher than baseline values. Urinary excretion of equol under these conditions has been shown to exceed 3.5 mg/day, which dwarfs the levels of the principal urinary estrogen excreted in urine in premenopausal women, estrone-glucuronide, typically excreted in amounts from 2 to 27 µg/day. Nonsteroidal Estrogens of Dietary Origin: Possible Roles in Hormone-Dependent Disease, K. Setchell et al., *Am. J Clin. Nut.*, 40: 569–78 (September 1984). The amount of equol which would be produced in response to the hormone replacement therapy of the '528 patent would only enhance the counterproductive effects of equol's relatively potent estrogencity in the therapy.

SUMMARY OF THE INVENTION

In one aspect, the invention is a composition for use in a hormone replacement therapy for a woman. The composition contains a combination of a mammalian estrogen and at least one isoflavone compound. The isoflavone compound is incapable of being metabolized to equol by a human. In a preferred embodiment the isoflavone is selected from genistein, genistin, 6"-O-malonylgenistin, 6"-O-acetylgenistin, glycitein, glycitin, 6"-O-malonylglycitin, biochanin A, and mixtures thereof.

In another aspect, the invention is a hormone replacement therapy regimen comprising co-administering a therapeutically effective amount of a combination of a mammalian estrogen and an isoflavone to a woman having reduced levels of endogenous estrogen, where the isoflavone is incapable of being metabolized to equol by a human. Preferably the hormone replacement therapy regimen is administered in an amount therapeutically effective to reduce the risk of cardiovascular disease, coronary heart disease, osteoporosis, declining mental cognition, urinary incontinence, weight and fat mass gain, and/or vasomotor symptoms. In a preferred embodiment, the isoflavone is selected from genistein, genistin, 6"-O-malonylgenistin, 6"-O-acetylgenistin, glycitein, glycitin, 6"-O-malonylglycitin, biochanin A, or a mixture thereof.

In a further aspect, the invention is a method for reducing the risk of cardiovascular disease, coronary heart disease, osteoporosis, loss of cognitive function, urinary incontinence, weight and fat mass gain, and/or vasomotor symptoms in a woman having reduced levels of endogenous estrogen wherein a therapeutically effective amount of a combination of a mammalian estrogen and an isoflavone are administered to the woman. The administered isoflavone is incapable of being metabolized to equol in a human. Preferably the isoflavone is selected from genistein, genistin, 6"-O-malonylgenistin, 6"-O-acetylgenistin, glycitein, glycitin, 6"-O-malonylglycitin, biochanin A, or mixtures thereof.

DESCRIPTION OF THE PREFERRED EMBODIMENTS

Figure 1:
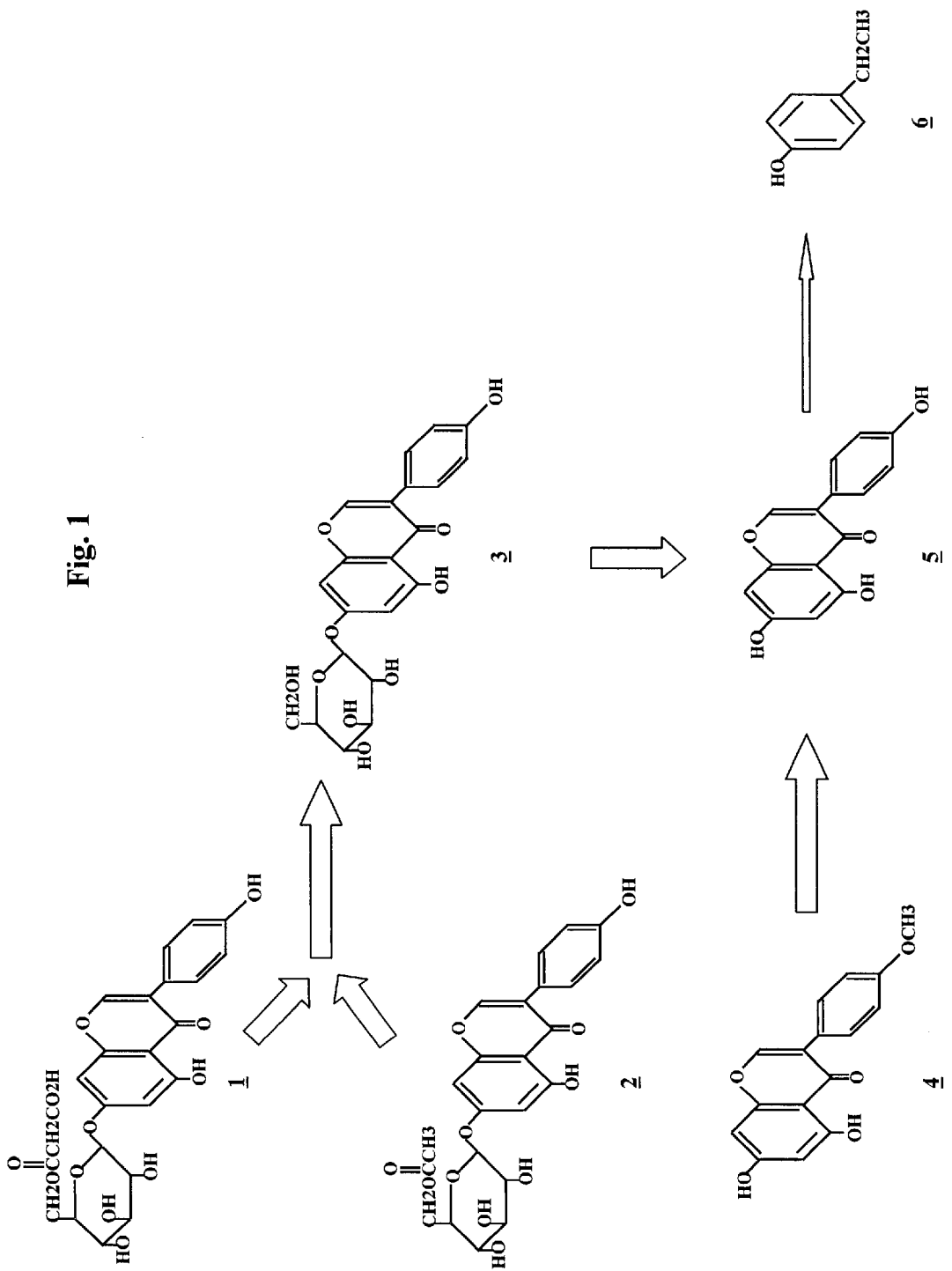
FIG. 1 is a depiction of the metabolic pathway of 6"-O-malonyl genistin, 6"-O-acetyl genistin, genistin, biochanin A, and genistein to p-ethylphenol.

As used herein, the term "hormone replacement therapy" means a treatment of a human female having reduced levels of endogenous estrogen in which a mammalian estrogen is administered to the female in combination with at least one other compound, where the other compound is administered to inhibit the estrogen's tissue proliferative effects in the breast or uterus. The term "mammalian estrogen" refers to a hormonal steroid endogenous in mammals which produces an estrogenic response at cellular estrogen receptors. As used herein, the term "reduced level of endogenous estrogen" refers to a human female serum concentration of estradiol which is at most 20 pg/ml. The term "metabolized" is used in accordance with its recognized meaning, e.g., the sum of processes by which a particular substance is assimilated, incorporated, detoxified, and/or excreted in a living body. The term "isoflavone" may mean both a single isoflavone or plural isoflavones when the isoflavone is defined as at least one of a selected group of isoflavones. The term "isoflavone glycoside" refers to a compound in which an isoflavone moiety and a glucose moiety are covalently bonded. The term "isoflavone glycoside conjugate" refers to an isoflavone glycoside having at least one additional moiety bound to the glucose portion of an isoflavone glycoside, for example, 6"-O-acetylgenistin contains an acetate group attached to the six position of the glucose molecule of genistin. As used herein "Mal" refers to malonyl and "Ac" refers to acetyl.

The present invention resides in the discovery that isoflavones which are incapable of being metabolized to equol by a human provide a safer and more effective alternative in a hormone replacement therapy for a woman having a reduced level of endogenous estrogen than a hormone replacement therapy utilizing an isoflavone composition which contains isoflavones that are metabolized to equol. Isoflavones are selective estrogen receptor modulators which have estrogenic activity in some body tissues, but importantly, have anti-estrogenic effects in breast and uterine tissues in the presence of estrogen. Certain isoflavones, however, are metabolized to equol, which is significantly more estrogenic than its precursor isoflavones or isoflavones which are incapable of being metabolized to equol.

The isoflavones utilized in the present composition and methods are incapable of being metabolized to equol. Administration of at least one of these isoflavones in combination with a mammalian estrogen provides the health benefits of estrogen and the desired protection of breast and uterine tissue from the tissue proliferative effect of estrogen without resulting in a metabolite which counteracts the estrogen antagonist effect of the isoflavones in the breast and uterus. The preferred isoflavones for use in the composition and methods of the present invention are selected from genistein, genistin, 6"-O-Mal genistin, 6"-O-Ac genistin, glycitein, glycitin, 6"-O-Mal glycitin, biochanin A, and mixtures thereof. These isoflavones are shown in Formulas 1 and 2 below.

Formula 1

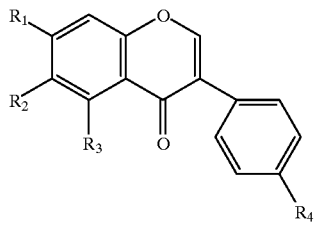

| Compound | $R_1$ | $R_2$ | $R_3$ | $R_4$ |
|---|---|---|---|---|
| Genistein | OH | H | OH | OH |
| Glycitein | OH | $OCH_3$ | H | OH |
| Biochanin A | OH | H | OH | $OCH_3$ |

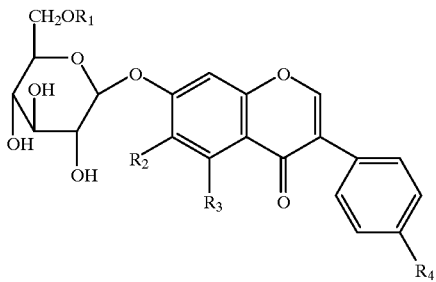

| Compound | $R_1$ | $R_2$ | $R_3$ | $R_4$ |
|---|---|---|---|---|
| Genistin | H | H | OH | OH |
| 6"-O-Mal genistin | $COCH_2CO_2H$ | H | OH | OH |
| 6"-O-Ac genistin | $COCH_3$ | H | OH | OH |
| Glycitin | H | $OCH_3$ | H | OH |
| 6"-O-Mal glycitin | $COCH_3$ | $OCH_3$ | H | OH |

Formula 2

Figure 2:
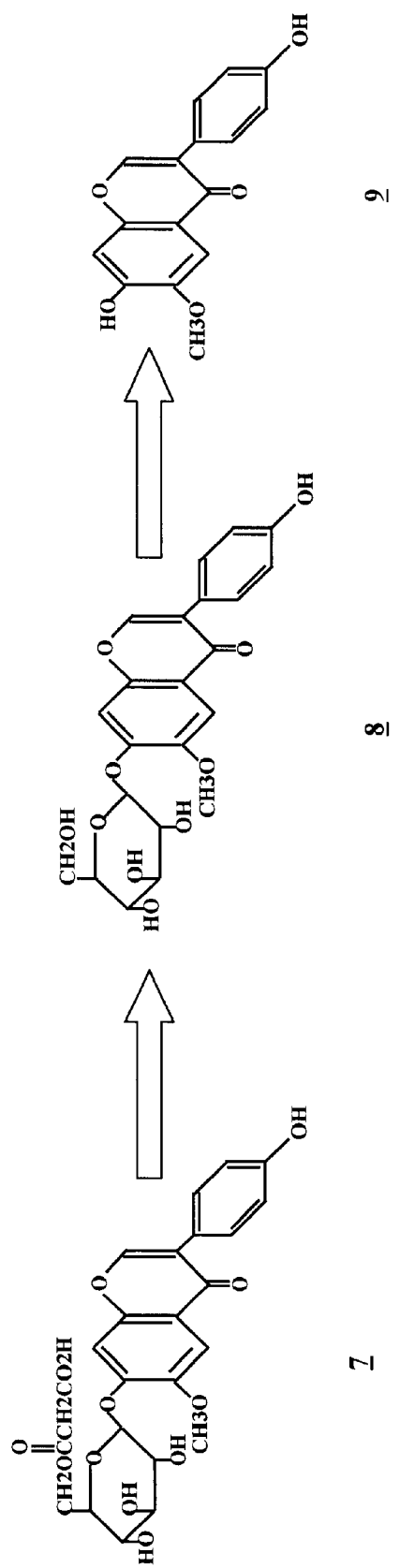
FIG. 2 is a depiction of the metabolic pathway of 6"-O-malonyl glycitin and glycitin to glycitein.
Figure 3:
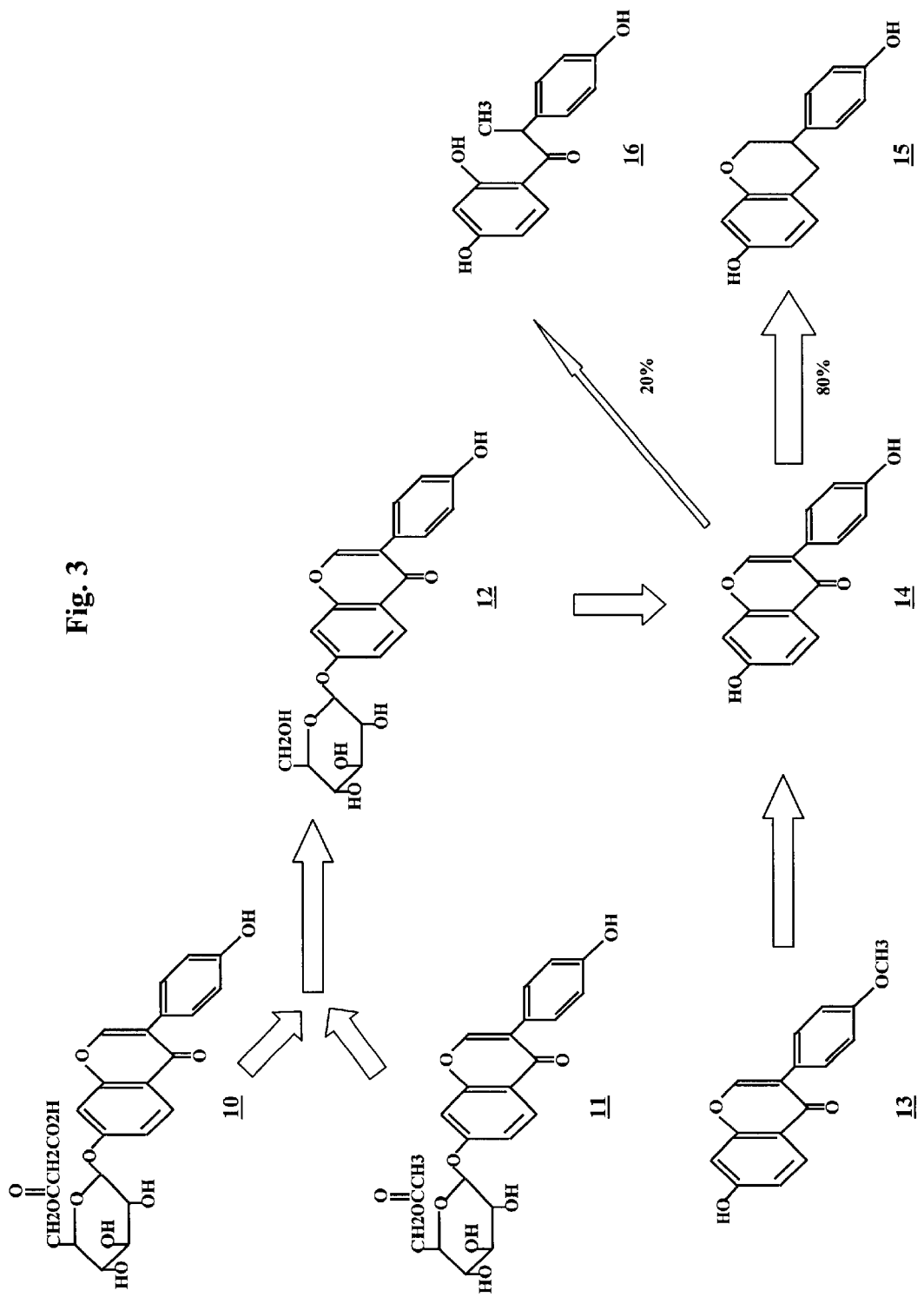
FIG. 3 is a depiction of the metabolic pathway of 6"-O-malonyl daidzin, 6"-O-acetyl daidzin, daidzin, formononetin, and daidzein to equol and o-desmethylangolensin.

As shown in FIG. 1, the isoflavone glycoside conjugates 6"-O-Mal genistin (1) and 6"-O-Ac genistin (2) are metabolized in humans to the isoflavone glycoside genistin (3), which is converted by gut flora into genistein (5). In humans, biochanin A (4) is demethylated to genistein (5). Some genistein (5) is metabolized to the hormonally inactive p-ethylphenol (6), and other genistein circulates through the body and is eventually excreted in the urine. As shown in FIG. 2, 6"-O-Mal glycitin (7) is metabolized to glycitin (8) which is metabolized to glycitein (9). The further metabolic pathway of glycitein is unclear, however, it is not converted to equol as a result of the methoxy group shown in the $R_2$ position in Formula 1 above.

Genistein, glycitein, biochanin A and their isoflavone glycosides and isoflavone glycoside conjugates are naturally occurring substances which are primarily found in legumes, clover, and the root of the kudzu vine (pureraria root). Common legume sources of these isoflavones include soybeans, chick peas, and various other types of beans and peas.

These isoflavones can be isolated from the plant sources in which they naturally occur for use in the composition and methods of the present invention. When isolating the desired isoflavones from a plant source care must be taken to separate these isoflavones from isoflavones which are capable of being metabolized to equol—daidzein, formononetin, and their naturally occurring glycosides and glycoside conjugates—at least one or more of which typically naturally occur in the same plants as the desired isoflavones. The metabolic pathway of formononetin, daidzein, and the naturally occuring daidzein glycosides and glycoside conjugates to equol is shown in FIG. 3—6"-O-Mal daidzin (10) and 6"-O-Ac daidzin (11) are metabolized to daidzin (12), and daidzin (12) and formononetin (13) are metabolized to daidzein (14), which is in turn metabolized to equol (15) and o-desmethylangolensin (16).

Preferably the desired isoflavones—genistein, glycitein, biochanin A, and their naturally occurring glycosides and glycoside conjugates—are isolated from a soy or a clover material. Soy materials from which the desired isoflavones can be isolated, except biochanin A which does not naturally occur in soy, include: solid soy materials such as whole soy beans, dehulled soy beans, soy meal, soy flour, soy grits, soy flakes (full fat and defatted), soy protein concentrate, soy protein isolate, and soy whey protein; and liquid soy extracts (which may include soy solids) such as soy molasses and soy whey. Clover materials from which the desired isoflavones can be isolated include subterranean clover and red clover.

If the plant material from which the isoflavones are to be separated is a solid non-particulated or non-flaked material such as whole soy beans, dehulled soy beans, or clover, the solid plant material is preferably initially comminuted into a finely divided form to facilitate extraction of the isoflavones from the plant material. The plant material may be comminuted according to conventional methods for comminuting vegetable or plant materials such as grinding, crushing, or shearing.

The desired isoflavones are extracted from a solid plant material with a solvent effective for solublizing the isoflavones from the plant material. Solvents which are particularly effective for extracting the isoflavones are low molecular weight alcohols, preferably methanol or ethanol; acetonitrile; ethyl acetate; acetone; chloroform; carbon tetrachloride; methylene chloride; water; or mixtures thereof. Preferably, the isoflavones are extracted from a solid plant material with an extractant containing water and an organic solvent, most preferably a 60% methanol: 40% water mixture.

To effect the extraction, the solid plant material is extracted with sufficient quantities of extractant to extract a majority, and preferably substantially all of the isoflavones from the plant material. Preferably the weight ratio of the extractant to solid plant material ranges from about 1:1 to about 20:1. Most preferably, the isoflavones are extracted from the solid plant material by refluxing the plant material in the extractant at the boiling point of the extractant for a period of from about 1 hour to about 5 hours.

Following extraction of the isoflavones, the extract containing the isoflavones is separated from the residual solid plant material. The extract may be separated from the residual plant material by conventional methods for separating solid and liquid phases. Preferably the separation is effected by centrifugation and collection of the supernatant, or by filtration and collection of the filtrate.

Preferably the separated extract is concentrated by evaporation under reduced pressure to form a syrup. The syrup is then extracted with acetone to separate the isoflavones from carbohydrates and protein which remain in the syrup. An acetone extract containing the isoflavones is then separated from the syrup by centrifugation or filtration.

The isoflavones may then be separated and collected from the acetone extract (or the initial extract if no acetone extraction is performed) by conventional reverse phase high performance liquid chromatography (HPLC). The extract is initially filtered to remove any insoluble materials that could plug an HPLC column. An HPLC column is prepared by packing a conventional commerically available HPLC column with a particulate adsorbent material which will releasably bind the desired isoflavones and undesirable isoflavones (which are capable of being metabolized to equol by a human) in a compound specific manner. The adsorbent material may be any reverse phase HPLC packing material or may be an anionic ion exchange resin. A preferred adsorbent material may be chosen by the criteria of load capacity, separation effectiveness, and cost. One such preferred packing material is Kromasil C18 16 μm 100 Å beads available from Eka Nobel, Nobel Industries, Sweden.

The filtered extract is passed through the packed HPLC column until all the binding sites of the column are fully saturated with isoflavones, which is detected by the appearance of isoflavones in the effluent from the column. The HPLC column may then be eluted with a solvent to effect separation of the desired isoflavones from the undesired isoflavones. Preferably, the eluent is a solvent selected from ethanol, methanol, ethyl acetate, acetonitrile, methylene chloride, water, or mixtures thereof. More preferably the eluent is an aqueous alcohol having an alcohol content of between about 30% to about 90% by volume, most preferably from about 40% to about 60% alcohol by volume.

The desired isoflavones—genistein, genistin, 6"-O-Mal genistin, 6"-O-Ac genistin, glycitein, glycitin, 6"-O-Mal glycitin, and biochanin A (if any)—may be separated and collected apart from the undesired isoflavones—daidzein, daidzin, 6"-O-Mal daidzin, 6"-O-Ac daidzin, and formononetin. The eluent fractions containing the desired isoflavones can be identified from other eluent fractions in accordance with conventional HPLC and analytical chemistry techniques. Of the aglycone isoflavone materials, the fraction of effluent containing the undesirable daidzein elutes first, followed by the desirable isoflavone fractions.

The fractions containing the desired isoflavones may be collected from the column and combined, and the volatile content of the solvent can be removed by evaporation. The isoflavones can be recovered directly if all the solvent is removed by evaporation, or may be recovered by chilling the remaining solvent (e.g. water) and centrifuging or filtering the isoflavones from the remaining solvent.

Most preferably, the isoflavone glycosides and isoflavone glycoside conjugates of the desired isoflavones and the undesired isoflavones are converted to their corresponding aglycone isoflavones before the separation of the isoflavones by HPLC to reduce the number of isoflavone compounds to be separated, thereby easing the separation and recovery of the desired isoflavones from the undesired isoflavones. The isoflavone glycosides and isoflavone glycoside conjugates are metabolized in the human body to their corresponding aglycones, therefore, conversion to the aglycone form prior to administration of the isoflavones in the hormone replacement therapy has no effect on the effectiveness of the hormone replacement therapy.

The conversion of the isoflavone glycoside conjugates and isoflavone glycosides to their corresponding aglycone isoflavones is preferably effected by forming a slurry of the solid plant material with water prior to the extraction of the isoflavones from the plant material. The isoflavone glycoside conjugates may be converted to their corresponding isoflavone glycosides by adding an alkali, preferably sodium or potassium hydroxide, to the slurry of plant material to adjust the pH of the slurry to a pH of from about 8 to about 13, and treating the aqueous alkaline slurry at a temperature of from about 25° C. to about 75° C. for period of about 30 minutes to about 5 hours. Substantially all of the isoflavone glycoside conjugates are converted to their corresponding isoflavone glycsosides at a pH of about 11 and a temperature of about 35° C. after a period of about 45 minutes.

Substantially all of the isoflavone glycosides in the plant material slurry can be converted to their corresponding aglycone isoflavones, preferably after converting the isoflavone glycoside conjugates to isoflavone glycosides. The isoflavone glycosides may be converted to their corresponding aglycone isoflavones by contacting the isoflavone glycosides with an enzyme capable of cleaving a 1,4-β-glycoside bond—preferably a commercially available β-glucosidase enzyme, an α- or β-galactosidase enzyme, a pectinase enzyme, a lactase enzyme, or a gluco-amylase enzyme—at a pH at which the enzyme is active, typically a pH from about 3 to about 9, and a temperature of from about 25° C. to about 75° C. for a perod of time sufficient to effect the conversion, typically from about 1 hour to about 5 hours.

After conversion of the isoflavone glycoside conjugates and isoflavone glycosides to their respective aglycone isoflavones, the aglycone isoflavones can be extracted from the plant material as described above. The water in the plant material slurry may be evaporated prior to extracting the plant material with an extractant, or the water may be utilized together with another solvent as the extractant.

If the plant material from which the desired isoflavones is to be separated is a liquid—e.g. soy molasses or soy whey—the isoflavones may be separated and recovered from the liquid plant material by filtering the liquid plant material to remove any solids in the liquid, and then separating the desired isoflavones by HPLC as described above. Alternatively, the liquid plant material may be filtered, concentrated and then extracted with acetone to provide an acetone extract containing the desired isoflavones. The isoflavones in the acetone extract may then be separated and recovered by HPLC as described above. Most preferably, the isoflavone glycoside conjugates and the isoflavone glycosides are converted to their respective aglycone isoflavones in the liquid plant material as described above prior to any extraction or separation of the isoflavones from the liquid plant material.

Alternatively, the isoflavones useful in the composition and method of the present invention may be prepared synthetically. Genistein may be synthetically prepared by the methods provided by Baker et al. (*J. Chem. Soc.,* p. 3115 (1928)); Narasimhadchari et al. (*J. Sci. Ind. Res.,* Vol. 12, p. 287 (1953)); Yoder et al. (Proc. *Iowa Acad. Sci.,* Vol. 61, p.271 (1954)); and Zemplen et al. (*Acta Chim. Acad. Sci. Hung.,* Vol. 19 p. 277 (1959)), each reference of which is incorporated herein by reference. Genistin may be synthetically prepared by the method of Zemplen et al. (*Ber.,* Vol 76B, p. 1110 (1943)), incorporated herein by reference. The isoflavone glycoside conjugates of genistin, 6"-O-Mal genistin and 6"-O-Ac genistin, can be prepared by conventional saponification of genistin with a malonyl or acetyl anhydride, respectively. Biochanin A may be synthetically prepared by the method provided by Baker et al. (*Nature,* Vol. 169, p. 706 (1952)), which is incorporated herein by reference.

Several of the isoflavone compounds useful in the composition and methods of the present invention are commercially available. For example, genistein and glycitein may be purchased from the Indofine Chemical Company, Inc., P.O. Box 473, Somerville, N.J. 08876, and biochanin A is available from the Aldrich Chemical Company, Inc., 940 West Saint Paul Avenue, Milwaukee, Wis. 53233.

The preferred mammalian estrogen for use in the composition and methods of the present invention is estra-1,3,5(10)-triene-3,17β-diol, shown in Formula 3 below, commonly known as estradiol. Estradiol is utilized as the estrogen component in conventional hormone replacement therapy, and is commercially available, e.g. as Estrace® from Mead Johnson, 2400 W. Lloyd, Evansville, Ind. Another mammalian estrogen that may be utilized in the composition and methods of the present invention is conjugated equine estrogen.

Formula 3

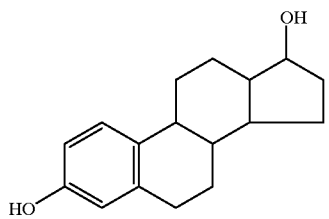

In one aspect, the present invention is a hormone replacement therapy regimen in which a therapeutically effective amount of a combination of a mammalian estrogen and an isoflavone are co-administered to a woman having reduced levels of endogenous estrogen, where the isoflavone is incapable of being metabolized to equol by a human. In a preferred embodiment, the isoflavone incapable of being metabolized to equol is selected from genistein, genistin, 6"-O-malonylgenistin, 6"-O-acetylgenistin, glycitein, glycitin, 6"-O-malonylglycitin, biochanin A, and mixtures thereof. These isoflavones may be obtained as described above.

Isoflavones and phytoestrogens which are capable of being metabolized to equol may be included in the hormone replacement therapy regimen, but should only be present in small amounts, typically as impurities derived from a plant material that are not completely separated from the isoflavones that are incapable of being metabolized to equol. The isoflavones and phytoestrogens capable of being metabolized to equol should only be present in the hormone replacement therapy regimen up to a level at which the hormone replacement therapy regimen produces an increase of urinary excretion of equol in a human of less than 500 μg/day. More preferably these isoflavones and phytoestrogens are only present in the hormone replacement therapy regimen in amounts such that the hormone replacement therapy regimen produces an increase of urinary excretion of equol in a human of less than 200 μg/day, and even more preferably less than 50 μg/day. Most preferably the hormone replacement therapy regimen contains no isoflavones and phytoestrogens which can be metabolized to equol, and the estrogen replacement therapy regimen produces no increase in the urinary excretion of equol.

In one aspect of the invention, the mammalian estrogen and the isoflavone which is incapable of being metabolized to equol in a human are utilized in a hormone replacement therapy regimen to inhibit or prevent coronary heart disease, cardiovascular disease, osteoporosis, loss of cognitive function, urinary incontinence, vasomotor symptoms, and/or weight gain and fat mass gain resulting from, or exacerbated by, a reduced level of endogenous estrogen. The mammalian estrogen serves to provide the protective effect against these diseases and conditions that endogenous estrogen provides prior to being reduced as a result of natural or surgically induced menopause. The isoflavone provides a protective anti-estrogenic effect against estrogen induced breast and uterine tissue proliferation, and supplements the mammalian estrogen's protective effects in other tissues without the production of substantial amounts of equol.

The combination of mammalian estrogen and isoflavone are administered to a woman having a reduced level of endogenous estrogen in a therapeutically effective amount to inhibit or prevent the development of these diseases or conditions. In a preferred embodiment of the invention, a therapeutically effective amount is from 0.2 mg/day to 5 mg/day of the mammalian estrogen, and from 20 mg/day to 1000 mg/day of the isoflavone which is incapable of being metabolized to equol. More preferably, a therapeutically effective amount of the mammalian estrogen is from 0.3 mg/day to 2 mg/day, and a therapeutically effective amount of the isoflavone is from 50 mg/day to 500 mg/day, and most preferably the mammalian estrogen is adminstered in an amount of from 0.5 mg/day to 1 mg/day and the isoflavone is administered in an amount of from 60 mg/day to 200 mg/day.

Although it is preferred that the mammalian estrogen and the isoflavone be adminstered on a daily basis, a therapeutically effective amount of these materials may be administered on a non-daily periodic basis, where the target dosage will be determined based upon the therapeutically effective daily dosages set forth above. For example, the mammalian estrogen may be administered every two days in a dosage of 0.4 mg, an average daily dose of 0.2 mg/day, while the isoflavone is administered daily in an amount of 20 mg/day. Any combination of regular periodic administration of the mammalian estrogen and the isoflavone may be utilized under the present invention, so long as the average daily dose of each compound is a therapeutically effective amount.

The mammalian estrogen and the isoflavone incapable of being metabolized to equol may be co-administered either concurrently or sequentially within the chosen period of time. Most preferably the mammalian estrogen and the isoflavone are co-administered concurrently in a composition of the present invention, as described below, on a periodic basis, preferably daily. Alternatively the mammalian estrogen and the isoflavone are administered sequentially as separate components. "Sequentially" as used herein is intended to mean administration of therapeutically effective amounts of the mammalian estrogen and the isoflavone individually within a specified periodic period of time, for example daily, and is not intended to be limited to immediate consecutive administration of the mammalian estrogen and the isoflavone.

The mammalian estrogen and the isoflavone which is incapable of being metabolized into equol may be formulated, separately or in combination, into formulations for administration in accordance with the present invention. The mammalian estrogen and the isoflavone may be formulated according to procedures known in the art into tablets, capsules, powders, solutions and suspensions for oral administration; suppositories for rectal administration; suspensions and solutions for parenteral administration including intravenous, intramuscular, and subcutaneous administration, and suspensions and solutions for application onto patches for transdermal application. The mammalian estrogen and isoflavone may then be administered, separately or in combination, orally, rectally, parenterally, or transdermally in accordance with the selected formulation.

In another aspect of the invention, the invention is a composition for use in a hormone replacement therapy regimen for a woman having reduced levels of endogenous estrogen. The composition contains a combination of a mammalian estrogen and at least one isoflavone which is incapable of being metabolized to equol by a human. Preferred isoflavones incapable of being metabolized to equol by a human for use in the composition include genistein, genistin, 6"-O-malonylgenistin, 6"-O-acetylgenistin, glycitein, glycitin, 6"-O-malonylglycitin, biochanin A, and mixtures thereof. The isoflavones may be derived from a plant source as described above, preferably soy or clover, may be prepared synthetically as described above, or may be acquired from a vendor of such materials. The preferred mammalian estrogen for use in the composition is estra-1, 3,5(10)-triene3,17β-diol, commonly known as estradiol.

The composition contains less than 10% by weight of isoflavones and phytoestrogens capable of being metabolized to equol by a human as active ingredients, and preferably contains less than 5% of isoflavones and phytoestrogens capable of being metabolized to equol, and more preferably contains less than 1% of these isoflavones and phytoestrogens. Most preferably the composition contains undetectable amounts of isoflavones and phytoestrogens which are capable of being metabolized to equol by a human.

A composition in accordance with the present invention containing a mammalian estrogen and an isoflavone incapable of being metabolized to equol can be prepared by conventional procedures for blending and mixing compounds. Preferably, the composition also includes an excipient, most preferably a pharmacuetical excipient. Compositions containing an excipient and incorporating the mammalian estrogen and isoflavone can be prepared by procedures known in the art. For example, the mammalian estrogen and the isoflavone can be formulated into tablets, capsules, powders, suspensions, solutions for parenteral administration including intravenous, intramuscular, and subcutaneous administration, and into solutions for application onto patches for transdermal application with common and conventional carriers, binders, diluents, and excipients.

Inert pharmaceutically acceptable carriers useful to form pharmaceutical compositions in accordance with the present invention include starch, mannitol, calcium sulfate, dicalcium phosphate, magnesium stearate, silicic derivatives, and/or sugars such as sucrose, lactose, and glucose. Binding agents include carboxymethyl cellulose and other cellulose derivatives, gelatin, natural and synthetic gums including alginates such as sodium alginate, polyethylene glycol, waxes and the like. Diluents useful in the invention include a suitable oil, saline, sugar solutions such as aqueous dextrose or aqueous glucose, and glycols such as polyethylene or polypropylene glycol. Other excipients include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents may also be added to the pharmaceutical compositions.

The composition is formulated with a therapeutically effective amount of the combination of mammalian estrogen and isoflavone to inhibit or prevent coronary heart disease, cardiovascular disease, osteoporosis, loss of cognitive function, urinary incontinence, vasomotor symptoms, and/or weight and fat mass gain in a woman having reduced levels of endogenous estrogen. A therapeutically effective amount of mammalian estrogen in the composition is from 0.2 mg to 5 mg, more preferably from 0.3 mg to 2 mg, and most preferably from 0.5 mg to 1 mg. A therapeutically effective amount of isoflavone in the composition is from about 20 mg to 1000 mg, more preferably from about 50 mg to 500 mg, and most preferably from about 60 mg to about 200 mg.

The following non-limiting formulations illustrate pharmaceutical compositions of the present invention. As used in the formulations "isoflavone" indicates one or more isoflavones which are incapable of being metabolized to equol by a human.

Formulations

The following Formulations 1–4 illustrate pharmaceutical formulations including a mammalian estrogen and an isoflavone.

Formulation 1
  Gelatin capsules
  Hard gelatin capsules are prepared using the following ingredients: estradiol 0.2–5 mg/capsule; Isoflavone 20–1000 mg/capsule; Starch, NF 0–600 mg/capsule; Starch flowable powder 0–600 mg/ capsule; Silicone fluid 350 centistokes 0–20 mg/capsule. The ingredients are mixed, passed through a sieve, and filled into capsules.

Formulation 2
  Tablets
  Tablets are prepared using the following ingredients: estradiol 0.2–5 mg/tablet; Isoflavone 20–1000 mg/tablet; Microcrystalline cellulose 20–300 mg/tablet; Starch 0–50 mg/tablet; Magnesium stearate or stearate acid 0–15 mg/tablet; Silicon dioxide, fumed 0–400 mg/tablet; silicon dioxide, colloidal 0–1 mg/tablet, and lactose 0–100 mg/tablet. The ingredients are blended and compressed to form tablets.

Formulation 3
  Suspensions
  Suspensions are prepared using the following ingredients: estradiol 0.2–5 mg/5 ml; Isoflavone 20–1000 mg/5 ml; Sodium carboxymethyl cellulose 50–700 mg/5 ml; Sodium benzoate 0–10 mg/5 ml; Purified water 5 ml; and flavor and color agents as needed.

Formulation 4
  Parenteral solutions
  A parenteral composition is prepared by stirring 1.5% by weight of active ingredients (estradiol and isoflavone wt/wt ratio of from 1:4 to 1:5000) in 10% by volume propylene glycol and water. The solution is made isotonic with sodium chloride and sterilized. cl EXAMPLES Example 1

A hormone replacement therapy regimen in accordance with the present invention is utilized to prevent or inhibit the development of atherosclerotic plaque, and thereby to inhibit or prevent the development of coronary heart disease and cardiovascular disease in postmenopausal women. Five to fifty women are selected for clinical study. The women are post-menopausal and have been diagnosed with atherosclerotic plaque including stenotic plaque and occlusive plaque. None of the women have utilized an estrogen replacement therapy for at least a year.

The women are divided into two groups, the first of which receives a daily dose of 0.625 mg of estrogen and 120 mg of genistein formulated into a pill tablet for oral administration (the "HRT" group), and the second of which receives a sugar pill placebo (the "Control" group). The diets of the groups are selected to contain no further source of isoflavones (such as soy), and no other source of estrogen is administered to either of the groups. The administration of the estrogen/genistein and placebo are continued for six months.

Prior to beginning adminstration of the estrogen/genistein or placebo, the patients are benchmarked for: high cholesterol levels; high density and low density lipoprotein cholesterol levels; estrogen levels; and degree of stenosis and atherosclerotic plaque in a selected blood vessel to be studied for vascular reactivity by non-invasive means (e.g., using high resolution ultrasound), preferably the superficial femoral artery or the brachial artery. The benchmarked indicators are measured again after the groups have been treated with the estrogen/genistein combination or placebo for six months. The results are compared between: 1) the HRT group prior to beginning the estrogen/genistein treatment and after 6 months of treatment; 2) the Control group prior to beginning the placebo treatment and after 6 months of treatment; and 3) the relative differences over the six month treatment period between the HRT group and the Control group. Enhanced anti-atherosclerotic activity, cardiovascular protective activity, and coronary heart protective activity of the hormone replacement therapy regimen and the composition of the present invention is shown by either a greater reduction in the total lipoprotein cholesterol level or low density lipoprotein cholesterol level, a greater increase in vascular reactivity, or a greater reduction of atherosclerotic plaque or stenosis in the HRT group relative to the Control group. Enhanced anti-atherosclerotic activity, cardiovascular protective activity, and coronary heart protective activity of the hormone replacement therapy regimen and the composition of the present invention is also shown by a significant reduction in total lipoprotein cholesterol level or low density lipoprotein cholesterol level, a significant increase in vascular reactivity, or a significant reduction of atherosclerotic plaque in the HRT group after six months of treatment with the estrogen/genistein composition relative to the HRT group prior to the treatment.

Utility of the hormone replacement therapy regimen and composition of the present invention for preventing or inhibiting coronary heart disease and cardiovascular disease is evidenced by activity of the estrogen/genistein composition in the above example relative to the placebo.

Example 2

A hormone replacement therapy regimen in accordance with the present invention is utilized to prevent or inhibit the progression of osteoporosis in postmenopausal women. Five to fifty women are selected for clinical study. The women are postmenopausal, having a plasma estradiol level of 20 pg/mL or less. None of the women have utilized an estrogen replacement therapy for at least a year.

Baseline values of urinary hydroxyproline, which is excreted during bone loss, and urinary creatine (creatine clearance), which is related to the rate of calcium excretion, are measured in the women. A baseline value of blood serum ionized calcium, an indicator of calcium level which, when low, indicates a probability of osteoporosis, is also measured in the women.

The women are then randomly divided into two groups, the first of which receives a daily dose of 0.625 mg of estrogen and 120 mg of genistein formulated into a pill tablet for oral administration (the "HRT" group), and the second of which receives a sugar pill placebo (the "Control" group). The diets of the groups are selected to contain no further source of isoflavones (such as soy), and no other source of estrogen is administered to either of the groups. The administration of the estrogen/genistein and placebo are continued for six months.

At the end of the six month treatment period the urinary hydroxyproline levels, urinary creatine levels, and the blood serum ionized calcium levels are measured in the women in the HRT group and in the Control group. The hydroxyproline/creatine ratio is calculated for the women of each of the groups, where the hydroxyproline/creatine ratio is a measure of the turnover of bone metabolism.

The resulting data is compared between: 1) the HRT group prior to beginning the estrogen/genistein treatment and after 6 months of treatment; 2) the Control group prior to beginning the placebo treatment and after 6 months of treatment; and 3) the relative differences over the six month treatment period between the HRT group and the Control group. Inhibition of osteoporosis is shown either by significantly higher ionized calcium levels and significantly lower hydroxyproline/creatine ratios in the HRT group relative to the Control group after the 6 month treatment period, or by maintenance of the initial baseline ionized calcium levels and hydroxyproline/creatine ratios in the HRT group throughout the 6 month treatment period Utility of the hormone replacement therapy regimen and composition of the present invention for preventing or inhibiting osteoporosis is evidenced by activity of the estrogen/genistein composition in the above example relative to the placebo, or by activity of the estrogen/genistein composition to maintain ionized calcium levels and hydroxyproline/creatine levels.

Example 3

A hormone replacement therapy regimen in accordance with the present invention is utilized to prevent or inhibit urinary incontinence in postmenopausal women. Five to fifty women are selected for clinical study. The women are post-menopausal, having a plasma estradiol level of 20 pg/mL or less, and having urodynamic evidence of genuine stress urinary incontinence in which the women suffer involuntary loss of urine at least once a week. None of the women have utilized an estrogen replacement therapy for at least a year.

For a period of six weeks the women record the number of incontinent episodes per week in a standardized urinary diary. Quantity of fluid loss and voluntary diurnal and nocturnal micturation frequency are also recorded.

The women are then randomly divided into two groups, the first of which receives a daily dose of 0.625 mg of estrogen and 120 mg of genistein formulated into a pill tablet for oral administration (the "HRT" group), and the second of which receives a sugar pill placebo (the "Control" group). The diets of the groups are selected to contain no further source of isoflavones (such as soy), and no other source of estrogen is administered to either of the groups. The administration of the estrogen/genistein and placebo are continued for six months.

Throughout the six month period of adminstration of the estrogen/genistein and placebo, the women in each group record the number of incontinent episodes per week in a standardized urinary diary. Quantity of fluid loss and voluntary diurnal and nocturnal micturation frequency are also recorded.

The resulting data is compared between: 1) the HRT group prior to beginning the estrogen/genistein treatment and after 6 months of treatment; 2) the Control group prior to beginning the placebo treatment and after 6 months of treatment; and 3) the relative differences over the six month treatment period between the HRT group and the Control group. Inhibition of urinary incontinence is shown either by a greater reduction in involuntary urinary episodes per week in the HRT group relative to the Control group, or by a significant reduction in involuntary urinary episodes per week in the HRT group at the end of the 6 month treatment period relative to the HRT group prior to the 6 month treatment period.

Utility of the hormone replacement therapy regimen and composition of the present invention for preventing or inhibiting urinary incontinence is evidenced by activity of the estrogen/genistein composition in the above example relative to the placebo.

Example 4

A hormone replacement therapy regimen in accordance with the present invention is utilized to prevent or inhibit loss of cognitive function in postmenopausal women. Five to fifty perimenopausal or postmenopausal women having mild to moderate Alzheimer's disease are selected for clinical study. The women are divided into two groups, one of which receives a daily dose of 0.625 mg of estrogen and 120 mg of genistein formulated into a pill tablet for oral administration (the "HRT" group), and the second of which receives a sugar pill placebo (the "Control" group). The diets of the two groups are selected to contain no further source of isoflavones, and no source of estrogen or androgen is administered to either of the two groups. The estrogen/ genistein and placebo treatments are continued for 6 months.

Prior to beginning the treatments patients are benchmarked as to cognitive ability. The benchmarked symptoms are measured again for each group after the groups have been on the diets for the prescribed period of the study. Activity of the estrogen/genistein treatment to aid in the preservation of cognitive function and to inhibit loss of cognitive function is shown by significant retention of cognitive function in the patients receiving the estrogen/ genistein treatment relative to the patients receiving the placebo.

Utility of the hormone replacement therapy regimen and composition of the present invention for inhibiting or preventing loss of cognitive function in a woman having reduced levels of endogenous estrogen is evidenced by activity of the estrogen/genistein composition in the above example.

Example 5

A hormone replacement therapy regimen in accordance with the present invention is utilized to prevent or inhibit vasomotor symptoms in perimenopausal women. Five to fifty women are selected for clinical study. The women are perimenopausal, having a plasma estradiol level of 20 pg/mL or less, and having symptoms of acute menopausal syndrome including at least an average of 3 hot flush episodes per day. None of the women have utilized an estrogen replacement therapy for at least a year.

For a period of six weeks the women record the number of hot flush incidents per day in a standardized diary. The women are then randomly divided into two groups, the first of which receives a daily dose of 0.625 mg of estrogen and 120 mg of genistein formulated into a pill tablet for oral administration (the "HRT" group), and the second of which receives a sugar pill placebo (the "Control" group). The diets of the groups are selected to contain no further source of isoflavones (such as soy), and no other source of estrogen is administered to either of the groups. The administration of the estrogen/genistein and placebo are continued for six months. Throughout the six month period of adminstration of the estrogen/genistein and placebo, the women in each group record the number of hot flush episodes per day in a standardized diary.

The resulting data is compared between: 1) the HRT group prior to beginning the estrogen/genistein treatment and after 6 months of treatment; 2) the Control group prior to beginning the placebo treatment and after 6 months of treatment; and 3) the relative differences over the six month treatment period between the HRT group and the Control group. Inhibition of vasomotor symptoms is shown either by a greater reduction in hot flush episodes per day in the HRT group relative to the Control group, or by a significant reduction in hot flush episodes per day in the HRT group at the end of the 6 month treatment period relative to the HRT group prior to the 6 month treatment period.

Utility of the hormone replacement therapy regimen and composition of the present invention for preventing or inhibiting vasomotor symptoms is evidenced by activity of the estrogen/genistein composition in the above example.

Example 6

A hormone replacement therapy regimen in accordance with the present invention is utilized to prevent or inhibit or prevent weight gain in perimenopausal and postmenopausal women. Five to fifty women are selected for clinical study. The women are perimenopausal or postmenopausal, having a plasma estradiol level of 20 pg/mL or less. The women do not smoke, do not use alcohol in excess, and are not on a weight reduction program. None of the women have utilized an estrogen replacement therapy for at least a year.

The women have their weight and body lean/fat mass ratio measured. The body lean/fat mass ratio is measured by bio-electrical impedance utilizing an Electrolipograph (BioAnalogics ELG, Beaverton, Oreg.) and the algorithmic formula set forth in U.S. Pat. No. 4,895,163, which is incorporated herein by reference in its entirety. The women are then randomly divided into two groups, the first of which receives a daily dose of 0.625 mg of estrogen and 120 mg of genistein formulated into a pill tablet for oral administration (the "HRT" group), and the second of which receives a sugar pill placebo (the "Control" group). The diets of the groups are selected to contain no further source of isoflavones (such as soy), and no other source of estrogen is administered to either of the groups. The administration of the estrogen/genistein and placebo are continued for six months. At the end of the six month period the weight and body lean/fat ratio of the women are re-measured.

The resulting data is compared between: 1) the HRT group prior to beginning the estrogen/genistein treatment and after 6 months of treatment; 2) the Control group prior to beginning the placebo treatment and after 6 months of treatment; and 3) the relative differences over the six month treatment period between the HRT group and the Control group. Inhibition or prevention of weight gain is shown either by significantly reduced weight gain in the HRT group relative to the Control group over the six month period of treatment, or by a significant reduction in weight in the HRT group at the end of the 6 month treatment period relative to the HRT group prior to the 6 month treatment period. Inhibition or prevention of fat mass gain is shown either by a significantly increased lean/fat mass ratio in the HRT group relative to the Control group over the six month period of treatment, or by a significant increase in the lean/fat mass ratio in the HRT group at the end of the six month treatment period relative to the HRT group prior to the six month treatment period.

Utility of the hormone replacement therapy regimen and composition of the present invention for preventing or inhibiting weight gain and fat mass gain is evidenced by activity of the estrogen/genistein composition in the above example

What is claimed is:

1. A composition for use in a hormone replacement therapy for a woman comprising a combination of mammalian estrogen and at least one isoflavone, wherein said isoflavone is incapable of being metabolized to equol by a human, and where said composition contains less than 10% by weight of isoflavones and phytoestrogens capable of being metabolized to equol by a human.

2. The composition of claim 1 wherein said isoflavone incapable of being metabolized to equol by a human is selected from genistein, genistin, 6"-O-malonylgenistin, 6"-O-acetylgenistin, glycitein, glycitin, 6"-O-malonylglycitin, biochanin A, and mixtures thereof.

3. The composition of claim 1 wherein said combination of mammalian estrogen and isoflavone are present in said composition in an amount sufficient to inhibit or prevent coronary heart disease and cardiovascular disease in a woman having reduced levels of endogenous estrogen.

4. The composition of claim 1 wherein said combination of mammalian estrogen and isoflavone are present in said composition in an amount sufficient to inhibit, reduce, or prevent osteoporosis in a woman having reduced levels of endogenous estrogen.

5. The composition of claim 1 wherein said combination of mammalian estrogen and isoflavone are present in said composition in an amount sufficient to inhibit or prevent loss of cognitive function in a woman having reduced levels of endogenous estrogen.

6. The composition of claim 1 wherein said combination of mammalian estrogen and isoflavone are present in said composition in an amount sufficient to inhibit or prevent urinary incontinence in a woman having reduced levels of endogenous estrogen.

7. The composition of claim 1 wherein said combination of mammalian estrogen and isoflavone are present in said composition in an amount sufficient to inhibit or prevent vasomotor symptoms in a woman having reduced levels of endogenous estrogen.

8. The composition of claim 1 wherein said combination of mammalian estrogen and isoflavone are present in said composition in an amount sufficient to inhibit or prevent weight gain and fat mass gain resulting from a reduced level of endogenous estrogen in a woman having reduced levels of endogenous estrogen.

9. The composition as in one of claims 3–8 wherein said composition contains from about 0.3–5 mg of mammalian estrogen and from about 20–1000 mg of isoflavone.

10. The composition of claim 1 wherein said mammalian estrogen is estradiol.

11. The composition of claim 1 wherein said isoflavone is derived from soy.

12. The composition of claim 1 wherein said isoflavone is derived from clover.

13. The composition of claim 2 wherein said isoflavone is prepared synthetically.

14. The composition of claim 1 wherein said composition contains less than 5% by weight of isoflavones and phytoestrogens capable of being metabolized to equol by a human.

15. The composition of claim 1 wherein said composition contains less than 1% by weight of isoflavones and phytoestrogens capable of being metabolized to equol by a human.

16. A hormone replacement therapy regimen comprising co-administering a therapeutically effective amount of a combination of mammalian estrogen and an isoflavone to a woman having reduced levels of endogenous estrogen, where said isoflavone is incapable of being metabolized to equol by a human, and where said hormone replacement therapy regimen produces an increase of urinary excretion of equol in a human of less than 500 µg/day.

17. The hormone replacement therapy regimen of claim 16 wherein said isoflavone is selected from genistein, genistin, 6"-O-malonylgenistin, 6"-O-acetylgenistin, glycitein, glycitin, 6"-O-malonylglycitin, biochanin A, and mixtures thereof.

18. The hormone replacement thereapy of claim 16 wherein said isoflavone is derived from soy.

19. The hormone replacement therapy of claim 16 wherein said isoflavone is derived from clover.

20. The hormone replacement therapy of claim 16 wherein said isoflavone is prepared synthetically.

21. The hormone replacement therapy regimen of claim 16 wherein said mammalian estrogen is estradiol.

22. The hormone replacement therapy regimen of claim 16 wherein the therapeutically effective amount is a daily dosage of about 0.3–5 mg of said mammalian estrogen and about 20–1000 mg of said isoflavone.

23. The hormone replacement therapy regimen of claim 16 wherein said mammalian estrogen and said isoflavone are administered concurrently.

24. The hormone replacement therapy regimen of claim 16 wherein said mammalian estrogen and said isoflavone are administered sequentially.

25. The hormone replacement therapy regimen of claim 16 wherein said estrogen replacement therapy regimen produces an increase of urinary excretion of equol in a human of less than 200 µg/day.

26. The hormone replacement therapy regimen of claim 16 wherein said estrogen replacement therapy regimen produces an increase of urinary excretion of equol in a human of less than 50 µg/day.

27. A method for inhibiting or preventing coronary heart disease, cardiovascular disease, osteoporosis, loss of cognitive function, urinary incontinence, weight gain and fat mass gain resulting from a reduced level of endogenous estrogen, or vasomotor symptoms in a woman having reduced levels of endogenous estrogen comprising administering to said woman a therapeutically effective amount of a combination of a mammalian estrogen and an isoflavone, where said isoflavone is incapable of being metabolized to equol in a human, and where administration of said mammalian estrogen and said isoflavone produces an increase in urinary excretion of equol in a human of less than 500 µg/day.

28. The method of claim 27 wherein the therapeutically effective amount is a daily dosage of about 0.3–5 mg of said mammalian estrogen and about 20–1000 mg of said isoflavone.

29. The method of claim 27 wherein said mammalian estrogen is estradiol.

30. The method of claim 27 wherein said isoflavone is selected from genistein, genistin, 6"-O-malonylgenistin, 6"-O-acetylgenistin, glycitein, glycitin, 6"-O-malonylglycitin, biochanin A, and mixtures thereof.

31. The method of claim 27 wherein said isoflavone is derived from soy.

32. The method of claim 27 wherein said isoflavone is derived from clover.

33. The method of claim 27 wherein said isoflavone is prepared synthetically.

34. The method of claim 27 wherein said mammalian estrogen and said isoflavone are administered concurrently.

35. The method of claim 27 wherein said mammalian estrogen and said isoflavone are administered sequentially.

36. The method of claim 27 wherein administration of said mammalian estrogen and said isoflavone produces an increase in urinary excretion of equol in a human of less than 200 µg/day.

37. The method of claim 27 wherein administration of said mammalian estrogen and said isoflavone produces an increase in urinary excretion of equol in a human of less than 50 µg/day.

* * * * *